United States Patent [19]

Wegman et al.

[11] Patent Number: 4,513,151
[45] Date of Patent: Apr. 23, 1985

[54] ACETALDEHYDE PROCESS

[75] Inventors: Richard W. Wegman, South Charleston; David C. Busby, Cross Lanes, both of W. Va.

[73] Assignee: Union Carbide Corporation, Danbury, Conn.

[21] Appl. No.: 557,271

[22] Filed: Dec. 2, 1983

[51] Int. Cl.³ ..................... C07C 45/49; C07C 45/50
[52] U.S. Cl. .................................. 568/484; 568/485; 568/489
[58] Field of Search ............... 568/484, 485, 489, 454

[56] References Cited

U.S. PATENT DOCUMENTS 4,302,611  11/1981  Porcelli ............................. 568/489
4,408,080  10/1983  Isogai et al. ....................... 568/485

FOREIGN PATENT DOCUMENTS 0046128  2/1982  European Pat. Off. ........... 568/484

Primary Examiner—Werren B. Lone
Attorney, Agent, or Firm—F. M. Fazio

[57] ABSTRACT

A process for the production of an aldehyde at high selectivity and rate by the reaction of an inorganic or organic ester with carbon monoxide or synthesis gas in contact with a catalyst system containing cobalt, rhodium or ruthenium atoms and lithium iodide and, optionally, an organic ligand.

24 Claims, No Drawings

ACETALDEHYDE PROCESS

BACKGROUND OF THE INVENTION

The production of organic compounds using carbon monoxide or synthesis gas, which is a mixture of carbon monoxide and hydrogen, as a reactant has been known for a significant period of time. It is well known that one can produce methanol directly from synthesis gas and that methanol can be further reacted by hydroformylation, homologation and carbonylation reactions to produce acetaldehyde, ethanol and acetic acid or its methyl ester, respectively. It is also known that esters, ethers, and other organic compounds can be reacted with carbon monoxide or synthesis gas to produce oxygenated organic compounds. The difficulties, however, have resided in the ability to carry out any one of these chosen reactions to produce the desired compound at acceptable efficiency, conversion rate and selectivity.

In almost all instances the reaction is generally catalyzed using a Group VIII transition metal compound as catalyst and a hologen as the promoter. It is known that many other metal compounds and promoters can be used. In addition, the prior art has disclosed the use of secondary activators or ligands in conjunction with the metal catalysts and promoters. These secondary activators can be other metallic salts or compounds, amines, phosphorus compounds, as well as a multitude of other compounds that have been disclosed in the published literature. Thus, a typical catalyst system contains the metal atom catalyst, promoter and, optionally, ligands, solvents and secondary activators. Though a significant amount of literature does exist describing the production of oxygenated organic compounds by the reaction of esters or alcohols with carbon monoxide or synthesis gas, to our knowledge it does not disclose or suggest our improved invention. Several of the pertinent patents in this area are discussed below.

In U.S. Pat. No. 3,356,734, issued to Kuraishi et al on Dec. 5, 1967, there is disclosed a process for producing acetaldehyde by the reaction of methanol with synthesis gas using a cobalt catalyst promoted by a halogen promoter. It contains no recognition of the benefits to be achieved with specific halogen promoters, nor does it suggest or disclose the use of initial reactants other than methanol.

The production of esters by the reaction of esters or ethers with synthesis gas is the subject of U.S. Pat. No. 4,189,441, issued to Braca et. al. on Feb. 19, 1980. The reaction is carried out using a ruthenium carbonyl and halogen promoter system. There is no specific mention of lithium iodide and there is obtained a mixture of many products; the reaction is not selective and aldehydes were not observed. In related articles, J. Am. Chem. Soc., 1978, 100, 6238, and Fundamental Research of Homogeneous Catalysis, Vol. 3, Plenum (1979), Braca et al state that no acetaldehyde was found among the products.

On Sept. 30, 1980, U.S. Pat. No. 4,225,517 was issued to Gane. This patent claims a process for reacting methanol with synthesis gas for the production of acetaldehyde in the presence of a cobalt catalyst, an iodine or bromine promoter, a compound of one of the elements arsenic, antimony or bismuth and the additional presence of an additive which can be an inert liquid, or an acid or acid derivative, or an oxygen-containing compound, or a non-polar solvent. The selectivities reported are below 60%. The patent contains no recognition of the unexpected and unpredictable benefits to be achieved by any single specific halogen compound. In column 10, lines 5 and 6, Gane indicates that the use of a trivalent phosphorus compound resulted in the production of ethanol as the major product rather than the production of acetaldehyde.

The Pretzer et. al. patent, U.S. Pat. No. 4,239,704, issued on Dec. 16, 1980, discloses a process for producing acetaldehyde by the reaction of methanol with synthesis gas using a system containing a cobalt entity, a ligand and an iodine compound. The reaction is non-selective, producing a mixture of many products, and exhibits a low selectivity to acetaldehyde and a relatively low conversion rate. Among the sources of halogen atom availability, lithium iodide is mentioned at column 4, line 24.

The reaction of methyl acetate with synthesis gas to produce acetic anydride is shown in U.S. Pat. No. 4,251,458, issued Feb. 17, 1981 to J. Pugach using a Group VIII noble metal component with a halogen component and an arsenic component. Though alkali metal halides are mentioned, there is no data supporting production of acetaldehyde. Nor does the patent contain any recognition of the benefits to be achieved by any specific halogen composition.

In Japanese Publications Nos. 77/136110, and 77/136111, filed by Saito et al and published on Nov. 14, 1977, there are disclosed cobalt catalysts promoted with an iodine compound and employing a phosphorus compound to react methanol with synthesis gas to produce acetaldehyde. In neither publication is there any mention of lithium iodide and both show low selectivities.

Japanese Publication No. 77/133914, filed by Saito et al and published on Nov. 9, 1977, relates to the reaction of methanol with synthesis gas to produce acetaldehydes using a system containing cobalt, a halide promoter and at least one element of the group, arsenic, antimony and bismuth. There is no disclosure of advantages to be gained from any specific halogen component and selectivities were low.

U.K. Patent Application No. 2,001,070A, filed by A. Saus and published on Jan. 24, 1979, relates to the homologation of esters with synthesis gas to produce a higher homolog of the charged ester. The catalyst system contains at least one of the metals cobalt, rhodium, ruthenium or iron and an iodine promoter. There is no suggestion or disclosure of the unexpected results to be achieved using lithium iodide.

The preparation of acetaldehyde by the reaction of methyl acetate with synthesis gas is the subject of U.K. patent application No. 2,038,829A filed by R. V. Porcelli and published on July 30, 1980. The catalyst system contains palladium, an iodine moiety (preferably methyl iodide), an organic promoter containing nitrogen, phosphorus, arsenic or antimony, and/or an inorganic promoter of elements having an atomic weight greater than 5 of Groups IA, IIA, IIIA, IVB, VIB and the non-noble metals of Group VIII. The reaction requires the use of the expensive palladium and excessive amounts of methyl iodide, a compound which is considered highly corrosive and thus very undesirable.

European Patent Application No. 0,025,702, published Mar. 25, 1981 and filed by Isshiki et al., pertains to the conversion of methyl acetate or dimethy ether to ethylidenediacetate using a system containing a nickel or cobalt compound and an iodine or bromine compound in conjunction with a promoter. Though LiI is disclosed as a suitable halide, it is not used in any of the examples, nor is there any suggestion or recognition of the unexpected results to be achieved by its use in the production of acetaldehyde from methyl acetate.

European Patent Application No. 0,031,784, published July 8, 1981, and filed by Gauthier-Lafaye et al., discloses a process for the homologation of esters to the next higher homolog. The catalyst system contains cobalt, ruthenium and iodine moieties; a combination of ionic and covalent halide is charged. A trace amount of acetaldehyde is reportedly produced as a by-product.

In German Offenlegungsschrift DE No. 2,941,232 Al, filed by Hans-Klaus et al., and published on Apr. 23, 1981, methyl acetate is reacted with synthesis gas using a system containing rhodium in combination with rhenium, manganese, or ruthenium, halogen compound, aliphatic carboxylic acid and a heterocycllic aromatic compound having a quarternary nitrogen atom. The principal product obtained was ethylidenediacetate; there is no indication that acetaldehyde could be made.

It can be seen that the prior art contains many disclosures dealing with the catalytic production of aldehydes via the reaction of alcohols and ethers with synthesis gas. In the reaction of an alcohol the accepted net reaction is:

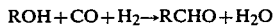

ROH+CO+H$_2$→RCHO+H$_2$O

One of the disadvantages in many of these references is the formation of water with the eventual need to remove it from the desired organic product. This removal is both complicated and costly. Other disadvantages often include the simultaneous occurrence of other reactions leading to the formation of by-products, such as, dimethyl acetal, methyl acetate, ethanol, etc. These reactions compete with the acetaldehyde production resulting in low acetaldehyde rate and selectivity.

Many processes employed for the production of aldehydes in the first stage and alcohols in the second reaction stage involve the reaction of an aldehyde with synthesis gas or carbon monoxide using a catalyst system containing a source of ruthenium and a source of halide present at least during the first stage. The alkali metal halides are often mentioned as suitable halide sources, but no distinction is made between any specific one of the alkali metal halides or between any other halogen compound. As with the use of methanol as the starting material, the use of formaldehyde also results in the formation of a mole of water, which must subsequently be removed. The formaldehyde-synthesis gas reaction can be shown as:

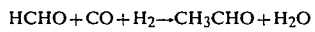

HCHO+CO+H$_2$→CH$_3$CHO+H$_2$O

SUMMARY OF THE INVENTION

A catalyst system and process for the production of an aldehyde at high efficiency, selectivity and conversion rate by the reaction of an ester with carbon monoxide or synthesis gas has been found. The catalyst charged to the reactor contains cobalt atoms, lithium iodide and optionally an organic ligand. The use of lithium iodide in this system within the ranges defined results in unexpectedly high efficiency, high conversion rate or activity and high selectivity not heretofore achieved, particularly in the production of essentially anhydrous aldehydes.

DESCRIPTION OF THE INVENTION

In the catalytic reactions of synthesis gas or carbon monoxide in processes to produce oxygenated organic compounds there are several criteria required of the catalyst. The catalyst must be as stable as possible, it should have a high activity or conversion rate, and it should have as high a selectivity for the desired product as possible.

Stability of the catalyst relates to how long the catalyst remains functional before either breaking down or losing its catalytic effect.

Activity or conversion rate relates to the amounts of reactants the catalyst converts to product per unit of time, generally expressed in g. mole per liter per hour (g mole/l/hr).

Selectivity relates to the quantity of desired product produced, generally expressed in mole percent, based on the total amount of both desired products and undesired products produced.

The goal to be achieved is high values for all three criteria and continued efforts are being made to find new catalyst compositions to reach this goal without having a significant detrimental effect on the overall process. Toward this goal the prior art has developed catalyst systems containing a wide variety of metal atoms, promoters and activators, in many cases with diverse other components added. Though these catalyst systems are effective, improvement is always desirable.

The present invention is based on the unexpected and unpredictable discovery that a metal-lithium iodide system in which the metal atom is cobalt, rhodium or ruthenium, or a mixture thereof is an unexpectedly superior catalytic system for the production of aldehydes from organic or inorganic esters at unexpected high selectivities and high conversion rates. In this application the symbol "Me" is used to represent said metals or metal atoms. It was also found that a ligand, ER$_3$''', can also be present as an optional component of the system. This unexpected improvement in both selectivity and conversion rate is achieved when the system's components are maintained within a defined range and when lithium iodide is present as the source of the halogen component in the system. Optionally a solvent and/or diluent can also be present. The improved catalyst system of this invention can be portrayed as containing the components Me-LiI-ER$_3$''', wherein Me is the cobalt, rhodium or ruthenium containing compound and ER$_3$''' is optionally present.

In the process of our invention organic or inorganic esters are reacted with carbon monoxide or synthesis gas using a particular system containing Me atoms and lithium iodide. This system produces commercially desirable aldehydes at unexpectedly high rates and selectivities, with a minimum of by-products and without formation of water. The reaction that occurs with a simple organic ester is theoretically:

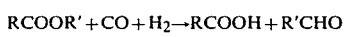

RCOOR'+CO+H$_2$→RCOOH+R'CHO

After separation of the two products, the RCOOH can be esterified with an alcohol R'OH and after drying the ester produced, RCOOR', it is recycled to the reactor. Thus, our process is one that essentially consumes only the alcohol, R'OH, in the production of the aldehyde, R'CHO, and recycling of the acid after removal of the aldehyde by adding the appropriate alcohol to the acid.

For example, if the initial organic ester is methyl acetate then the products formed are acetaldehyde and acetic acid; water is not formed in our process. The acetaldehyde is removed and in a separate reaction the methyl acetate is regenerated by the esterification of the acetic acid with added methanol. The water produced in the esterfication is removed and the methyl acetate is cycled to the reactor. Thus, pure acetaldehyde is produced with the net reaction being conversion of methanol into acetaldehyde. In this process the acid is not consumed and it is present only as a carrier or transferring agent. Further, in this process anhydrous conditions exist during the reaction, thus minimizing equipment corrosion, and product separation and purification procedures.

Alternatively, the desired ester feedstock can be generated in situ in the reactor. For example, if acetaldehyde is desired then a methyl ester can be generated by co-feeding methanol and a carboxylic acid to the reactor. In this case, however, the water formed remains in the reactor and essentially anhydrous conditions would not prevail thus possibly negating one of the advantages of this invention, namely conducting the reaction under essentially anhydrous conditions.

The organic ester RCOOR' consists of a carboxylic acid fragment RCO- and an alcohol fragment —OR'. As long as the —OR' fragment remains the same the same aldehyde is produced from any ester regardless of the carboxylic acid fragment. For instance, acetaldehyde would be produced from any methyl ester, e.g., methyl acetate, methyl propionate, methyl butyrate, etc., and the respective acid would be acetic acid, propionic acid, butyric acid, etc., thus affording flexibility in the carboxylic acid produced and in the esterification step since some acids may be easier to esterify than others. One can also use compounds having more than one ester linkage, for example, R'OOCR"COOR' esters, in which R" is a divalent hydrocarbyl group of the types defined for R and R' but having from 2 to 10 carbon atoms.

In the above formulas R and R' can be the same or different monovalent hydrocarbyl groups and can be an alkyl group having from 1 to 30 carbon atoms, preferably from 1 to 15 carbon atoms most preferably 1 to 5 carbon atoms; an alkenyl group having from 2 to 30 carbon atoms, preferably from 2 to 15 carbon atoms most preferably 2 to 5 carbon atoms; or an aryl, aralkyl or alkaryl group having 6 or 10 ring carbon atoms, e.g., phenyl or naphthyl, which can be substituted with groups having from 1 to 10 carbon atoms in the alk- moiety thereof. The R and R' groups can be linear or branched and they can be unsubstituted or substituted with groups which will not have an adverse effect on the reaction; further; the alkenyl groups can contain more than one unsaturated bond. R can also be hydrogen.

Illustrative of suitable esters one can mention methyl formate, ethyl formate, isobutyl formate, methyl acetate, ethyl acetate, the propyl acetates, the butyl acetates, the decyl acetates, 2-ethylhexyl acetate, stearyl acetate, phenyl acetate, benzyl acetate, vinyl acetate, allyl acetate, methyl propionate, ethyl propionate, isopropylpropionate, methyl butyrate, ethyl butyrate, isopropyl butyrate, methyl benzoate, propyl benzoate, methyl salicylate, iso-propyl salicylate, dimethyl malonate, diethyl malonate, dimethyl succinate, diisopropyl succinate, dimethyl maleate, dimethyl phthalate, diisobutyl phthalate, methyl cinnamate, iso-butyl cinnamate.

The inorganic esters are well known to those of ordinary skill; the preferred inorganic esters are the borate esters of the general formula $B(OR'''')_3$ in which the R'''' groups can be the same or different in the molecule and are alkyl groups, linear or branched, substituted or unsubstituted, having from 1 to 15 carbon atoms, preferably 1 to 4 carbon atoms. Illustrative of suitable borate esters one can mention trimethyl borate, triethyl borate, methyl diethyl borate, tripropyl borate, tributyl borate, tridecyl borate, tri-2-ethylhexyl borate, tripentadecyl borate.

The rhodium atom as the Me component of the catalyst system can be supplied from any number of sources, many of these are known to those of ordinary skill in the art. Thus, it is not necessary for an understanding thereof to specifically enumerate every suitable type and every specific compound since any of the known rhodium compounds can be used.

The rhodium atom of the catalyst system of the present invention may be provided by introducing into the reaction zone a compound of rhodium or may be provided by introducing into the reaction zone rhodium itself or any mixture of these. Among the materials which may be charged to the reaction zone to provide the rhodium component of the catalyst system of the present invention are rhodium metal, rhodium salts and oxides, organo rhodium compounds, coordinated compounds of rhodium, and the like. Specific examples of materials capable of providing the rhodium constituent of the catalyst system of the present invention may be taken from the following non-limiting partial list of suitable materials.

$RhCl_2$
$RhBr_3$
$RhI_2$
$RhCl_3 \cdot 3H_2O$
$RhBr_3 \cdot 3H_2O$
$Rh_2(CO)_4Cl_2$
$Rh_2(CO)_4Br_2$
$Rh_2(CO)_4I_2$
$Rh_2(CO)_8$
$Rh[(C_6H_5)_3P]_2(CO)I$
$Rh[(C_6H_5)_3P]_2(CO)Cl$
Rh metal
$Rh(NO_3)_3$
$RhCl[(C_6H_5)_3P]_2(CH_3I)_2$
$Rh(SnCl_3)[(C_6H_5)_3P]_2$
$RhCl(CO)[(C_6H_5)_3As]_2$
$RhI(CO)[(C_6H_5)_3Sb]_2$
$[(n-C_4H_9)_4N][Rh(CO)_2X_2]$ where X = Cl—, Br—, I—
$[(n-C_4H_9)_4As]_2[Rh(CO)_2Y_2]$ where X = Br—, I—
$[(n-C_4H_9)_4P][Rh(CO)I_4]$
$Rh[(C_6H_5)_3P]_2(CO)Br$
$Rh[(n-C_4H_9)_3P]_2(CO)Br$
$Rh[(n-C_4H_9)_3P]_2(CO)I$
$RhBr[(C_6H_5)_3P]_3$
$RhI[(C_6H_5)_3P]_3$
$RhCl[(C_6H_5)_3P]_2$
$RhCl[(C_6H_5)_3P]_3H_2$
$[(C_6H_5)_3P]_3Rh(CO)H$
$Rh_2O_3$
$[Rh(C_3H_4)_2Cl]_2$
$K_4Rh_2Cl_2(SnCl_2)_4$
$K_4Rh_2Br_2(SnBr_3)_4$
$K_4Rh_2I_2(SnI_2)_4$ The ruthenium atom as the Me component of the catalyst system can come from any source which is capable of providing ruthenium atoms in the reaction; these are well known to those of ordinary skill in this art. Illustrative of such ruthenium compounds one can name ruthenium trichloride, ruthenium tribromide, ruthenium triiodide, ruthenium acetate, ruthenium acetylacetonate, ruthenium propionate, ruthenium octanoate, ruthenium dioxide, ruthenium tetraoxide, ruthenium pentacarbonyl, triruthenium dodecacarbonyl and the like. Convenient sources of ruthenium are ruthenium trichloride and triruthenium dodecacarbonyl. Mixtures of ruthenium compounds can be used.

The cobalt atom as the Me component of the catalyst system can be supplied from any number of sources, many of these are known to those of ordinary skill in the art. Thus, it is not necessary for an understanding thereof to specifically enumerate every suitable type and every specific compound since any of the known compounds can be used. Nevertheless, descriptive of some of the useful cobalt sources are the known cobalt carboxylates such as cobalt formate, cobalt acetate, cobalt benzoate, cobalt toluate, cobalt propionate, cobalt butyrate, cobalt valerate, cobalt hexanoate, cobalt cyclohexylbutyrate, and the like; the cobalt carbonyls such as dicobalt octacarbonyl, acetyl cobalt tetracarbonyl, tricobalt dodecacarbonyl, and the like, including their phosphine substituted analogs many of which are known to those skilled in the art; the cobalt oxides such as cobalt oxide; cobalt hydroxide; cobalt halides such as cobalt iodide; cobalt carbonate; cobalt bicarbonate; cobalt. Any of the known cobalt complexes can also be used; for example, those of the type $Co(X)_n(ER_3''')_m$ in which X is a halogen atom and $ER_3'''$ is as hereinafter defined. Mixtures of cobalt compounds can be used. When a cobalt halide is used, proper adjustment is required to maintain the cobalt halide ratio as defined in this invention. One can also use any mixture containing cobalt, rhodium or ruthenium atoms.

The Me atom concentration can vary over a wide range. Enough Me atom must be present in order to achieve reasonable reaction rates; however, excess Me can result in undesired by-products formation. The mole ratio of Me to ester can vary from 1:25 to 1:2,000, the preferred range is from about 1:50 to 1:500, with the most preferred range being from about 1:100 to 1:400.

The second component of the catalyst system is lithium iodide. It can be charged directly, or it can be formed in situ by any combination of lithium compound and iodine component that will result in the formation of lithium iodide during the reaction. Lithium bromide can also be used but the iodide is preferred. The presence of lithium iodide or lithium bromide is a critical feature of this invention. Direct charge of lithium iodide is the preferred form; however, a convenient combination for in situ formation of lithium iodide can be used. This includes the use of lithium carboxylates, carbonates and the like with a halogen compound. A suitable combination for in situ formation is lithium carboxylate and an alkyl halide. It is preferable to use a lithium carboxylate salt having the same organic moiety as the ester feedstock and methyl iodide when a methyl ester is used.

Sufficient lithium iodide must be present to exert a promoting effect on the reaction and to result in high conversion rates and selectivities to the corresponding aldehyde. The mole ratio of LiI:Me can vary over a wide range. A LiI:Me mole ratio of from 50:1 to 1:50 can be economically employed, the preferred range is from about 10:1 to 1:10 and most preferably is from about 3:1 to 5:1.

As indicated, an organic ligand of the general formula $ER_3'''$ can optionally be present in the reaction system. The use of such ligands is known, as are their identities, to those skilled in this art. In this formula E represents a Group VA element, e.g., N, P, As, Sb and Bi, and $R'''$ represents an organic moiety. The ligand serves as a catalyst stabilizer and/or to further enhance efficiency, conversion rate and selectivity, especially when the reaction is carried out at higher temperatures, for example at about 200° C. or above. The ligand also serves to inhibit equipment corrosion in some instance. However, the use of a ligand is not mandatory and the reaction can be carried out without it.

A large number of organic ligands is known and any of these can be used provided they do not have an adverse effect on the reaction. Among those of particular utility are the tertiary amines and the tri- and pentavalent phosphorus compounds. Though those skilled in the art know these compounds, illustrative of suitable compounds one can mention triethylphosphine, tributylphosphine, tri-2-ethylhexylphosphine, triphenylphosphine, tri(4-methoxyphenyl)phosphine, tri-p-tolylphosphine, tri(3-chlorophenyl)phosphine, diphenyl hexylphosphine, dimethyl (3-methoxyphenyl)phosphine, dibutyl stearylphosphine, tribenzylphosphine, dipropyl phenylphosphine, ethyl dipropylphosphine, tricyclohexylphosphine, cyclohexyl dibutylphosphine, propyl diphenylphosphine, dipropyl phenylphosphine, phenyl diethylphosphine, tridecylphosphine, trioctadecylphosphine, tribenzylphosphine, methyl diethylphosphine, ethyl diphenylphosphine, tolyl diethylphosphine, cyclohexyl diethylphosphine, diethyl cyclohexylphosphine, bis-(diphenylphosphino)ethane, bis-(diethylphosphine)-propane, bis-(diphenylphosphino)-butane, bis-(diethylphosphino)octane, trimethylamine, triethylamine, tri-n-butylamine, tri-t-butylamine, tri-2-ethylhexylamine, methyl dibutylamine, tridodecylamine, tristearylamine, ethyl dibutylamine, tricyclohexylamine, triphenylamine, tri(4-methoxyphenyl)amine, tri(p-chlorophenyl)-amine, dibutyl phenylamine, dipentyl cyclopentylamine, ethyl diphenylamine, trinaphthylamine, tri-p-tolylamine, tri-benzylamine, tri(3-methylcyclohexyl)amine, and the arsines, stibines and bismuthines corresponding to the above-identified phosphines and amines. These and many others are known in the art. They can be used singly or, if one desires, mixtures containing two or more ligands can be used. One can also employ a phosphine oxide or phosphite corresponding to the above phosphines as the ligand; these are also well known.

The concentration of ligand charged can vary from a molar ratio of ligand to Me atom of about 50:1 to 1:50, preferably from 10:1 to 1:10, most preferably about 3:1 to 1:1.

In addition to the ligand one can optionally have a solvent present. Many solvents are known as useful, essentially inert, diluents and illustrative thereof one can mention 1,4-dioxane, the polyethylene glycol di-ethers or esters, diphenyl ether, sulfolane, toluene, carboxylic acids (especially the carboxylic acid used in the organic ester feedstock), as well as any other diluent or solvent which does not interfere with the reaction to any significant extent. The reaction is preferably carried out in the absence of any solvent or diluent other than those required to introduce reactants or catalyst components.

The reaction is carried out at a temperature of from about 100° C. to 300° C., preferably from 140° C. to 250° C. and most preferably from 150° C. to 225° C.

The pressure of the reaction can be from about 500 psig to 10,000 psig and preferably from 1,000 psig to 6,000 psig.

The mole ratio of $H_2:CO$ in the synthesis gas feed mixture can range from 1:10 to 10:1, preferably from 5:1 to 1:5 and most preferably from 2:1 to 1:2. As previously indicated carbon monoxide itself can be used.

The reaction time varies depending upon the reaction parameters, reactor size and charge, and the individual components employed at the specific process conditions. The reaction can be a batch or continuous reaction.

The experiments and examples detailed below were carried out in a Hasteloy ® steel autoclave reactor having a volume of 300 ml, which was equipped with temperature and pressure sensing means, heating and cooling means, agitator and inlet and outlet means for introducing and removing components from the reactor. The autoclaves used in the synthesis gas reactions are well known in the art and can be used in this process.

Prior to charging the reactants the autoclave was washed with methanol at 100° C. under a synthesis gas pressure of 500 to 1,000 psig by agitating for 30 minutes. The autoclave was drained, rinsed with dry acetone, and dried with nitrogen. The liquid components were charged to the cleaned autoclave first and then the solid components were added and stirred. The autoclave was closed, purged with carbon monoxide or synthesis gas and then pressurized with carbon monoxide or synthesis gas. The autoclave contents were heated to the selected temperature, with agitation (usually 750 rpm), in about 45 minutes. As soon as the desired temperature was reached, the autoclave was brought to the desired pressure plus 250 psig. The reaction was allowed to consume carbon monoxide or synthesis gas until the pressure had fallen to 250 psig below the desired pressure. The reactor was then repressurized to 250 psig above the desired pressure. One such cycle is considered 500 psig gas uptake. Unless otherwise specified the reactions were allowed to proceed until 3,000 psig carbon monoxide or synthesis gas uptake had occurred.

At the end of a reactor run, the contents were cooled, generally to about 10° C. A vapor phase sample was taken for gas chromatography analysis; the gas phase was vented through two dry-ice acetone traps and then through a 10 liter saturated solution of calcium hypochlorite to remove metal carbonyls. The reactor was pressurized three times with nitrogen, 90 psig, and vented through the same system.

The residual reactor contents were dumped into a chilled pressure bottle and sealed. Subsequent analysis was performed using a Hewlett-Packard Model 5880 gas chromatograph equipped with two columns one-eighth inch in diameter by ten feet long connected in series. The columns were packed with Chromosorb 101.

The following examples serve to further illustrate this invention. In all examples conversion rates and selectivities include acetaldehyde plus the acetaldehyde equivalents in dimethylacetal or paraldehyde.

EXAMPLE 1

The autoclave was charged with 2.5 g of cobaltous iodide (8 mmoles), 3.49 g of tributylphosphine oxide (16 mmoles), 4.28 g of lithium iodide (32 mmoles) and 150 ml of methyl acetate (1.9 moles). Following the procedure described above the reactor contents were heated to 160° C. and the pressure adjusted to 5,000 psig using a $H_2:CO$ mixture having a 1:1 mole ratio. The reaction commenced upon pressuring to about 5,000 psig as evidenced by constant uptake of gas and was continued for 80 minutes at 5,000±250 psig for a total gas consumption of 3,000 psig. The reactor was then cooled and treated as described above. Analysis indicated the following products were produced:

Acetaldehyde: 0.18 mole
Paraldehyde: 0.06 mole
Acetic acid: 0.34 mole
Methane: 0.01 mole
Water: 0.03 mole
Ethyl acetate: Trace The remainder of the product mixture removed from the reactor was unreacted methyl acetate that had not been given adequate time to react. The rate to acetaldehyde was 1.83 gmoles/L/hr (includes acetaldehyde equivalents in the paraldehyde) and the rate to acetic acid was 1.75 gmoles/L/hr. The selectivity to acetaldehyde is about 95%, excluding acetic acid.

The example shows the excellent material balance and selectivity to acetaldehyde that are achieved. Theoretically one would expect the acetic acid: total acetaldehyde equivalents molar ratio to be 1:1; in this instance it is 1:1.06. The 95% selectivity achieved is also exceptionally good. Further, the production of very few by-products and at low concentrations is a distinct advantage.

EXAMPLE 2

The autoclave was charged with 2.5 g of cobalt iodide (8 mmoles), 5.9 g of tributylamine (32 mmoles), 6.42 g of lithium iodide (48 mmoles) and 150 ml. of methylacetate (1.9 moles). The same procedures were utilized as described in Example 1 with the exception that the reaction temperature was 170° C. Consumption of 3,000 psig of gas required 41 minutes. Analysis indicated the following products were produced:

Acetaldehyde: 0.33 mole
Ethyl acetate: 0.004 mole
Acetic acid: 0.35 mole
Water: 0.06 mole
Dimethyl acetal: 0.004 mole The unreacted methyl acetate was recovered. The results further support the excellent material balance and selectivity to acetaldehyde that are achieved by the use of lithium iodide as the source of the halogen component. The selectivity to acetaldehyde is about 94%, excluding acetic acid. The rate to acetaldehyde was 3.2 gmoles/L/hr and the rate to acetic acid was 3.58 gmoles/L/hr. As in Example 1, by-products formation was insignificant.

EXAMPLE 3

The autoclave was charged with 2.5 g of cobaltous iodide (8 mmoles), 3.92 g of triphenylamine (16 mmoles), 4.28 g of lithium iodide (32 mmoles) and 150 ml of methyl acetate and reacted at 200° C. in the manner described in Example 1. The consumption of 3,000 psig of gas required 23 minutes. Analysis indicated the following products were produced:

Acetaldehyde: 0.2 mole
Paraldehyde: 0.07 mole
Acetic acid: 0.3 mole
Methane: 0.01 mole
Water: 0.06 mole
Ethyl acetate: 0.008 mole The unreacted methyl acetate was recovered. The rate to acetaldehyde was 7.01 gmoles/L/hr (includes acetaldehyde equivalents in the paraldehyde). The selectivity to acetaldehyde remained unaffected at about 95%, excluding acetic acid.

EXAMPLE 4

A two-run series was carried out in a manner similar to that described in Example 1 using diphenyl ether as solvent. In each instance the autoclave was charged with 2.5 g of cobaltous iodide (8 mmoles), 4.28 g of lithium iodide (32 mmoles), 100 ml of methyl acetate (1.27 moles) and 50 ml of diphenyl ether. Run A contained 1.48 g of tributylamine (8 mmoles) and was carried out at 180° C. Run B contained 1.96 g of triphenylamine (8 mmoles) and was carried out at 200° C. Analysis indicated the following results:

| RUN | A | B |
|---|---|---|
| Acetaldehyde, mole | 0.16 | 0.2 |
| Paraldehyde, mole | 0.06 | 0.07 |
| Acetic acid, mole | 0.30 | 0.33 |
| Methane, mole | 0.01 | 0.03 |
| Water, mole | 0.05 | 0.07 |
| Ethyl acetate, mole | 0.01 | 0.01 |
| Rate (a) | 2.83 | 4.36 |
| Selectivity, % (b) | 94 | 91 |

(a) gmoles/L/hr to acetaldehyde, includes acetaldehyde equivalents in paraldehyde
(b) excludes acetic acid.

The presence of a solvent has no significant effect on rate, selectivity, by-products formation, or materials balance.

EXAMPLE 5

In this series, water and a mixture of water and acetic acid were used as the inert solvent. In both instances the autoclave was charged with 2.5 g of cobaltous iodide (8 mmoles), 4.28 g of lithium iodide (32 mmoles) and 2.96 g of tributylamine (16 mmoles). Run A contained 115 ml of methyl acetate, 15 ml of water and 20 ml of acetic acid; the reaction temperature was 170° C. Run B contained 130 ml of methyl acetate and 20 ml of water; the reaction temperature was 180° C. Both examples were carried out in a manner similar to that described in Example 1. Analysis indicated the following results:

| RUN | A | B |
|---|---|---|
| Acetaldehyde, mole | 0.15 | 0.3 |
| Paraldehyde, mole | 0.01 | 0 |
| Acetic acid, mole | (a) | 0.8 |
| Methane, mole | 0.01 | 0.02 |
| Ethyl acetate, mole | 0.01 | 0.03 |
| Rate (b) | 0.75 | 1.5 |

(a) not determined due to acetic acid charged
(b) gmoles/L/hr to acetaldehyde, includes acetaldehyde equivalents in paraldehyde The results show that the presence of water with the catalyst system of this invention has little adverse effect on selectivity. This was completely unexpected and unpredictable when consideration is given to the disclosure on page 2, lines 33 to 39 of U.K. Patent Application No. 2,038,829A in which it was stressed that the system should be substantially free of water and that the presence of more than 5 mole percent of water should be avoided. In Example 5, Run A contained about 32 mole percent added water and Run B contained about 41 mole percent added water based on the amounts of methyl acetate, acetic acid and water initially charged.

EXAMPLE 6

A series of experiments was run under conditions similar to those described in Example 1. In all instances the autoclave was charged with 1.42 g of cobaltous acetate (8 mmoles) and 150 ml of methyl acetate. Run A contained 2.96 g of tributylamine (16 mmoles) and 4.28 g of lithium iodide (32 mmoles); the reaction was carried out at 180° C. for 0.9 hour. Run B contained 3.92 g of triphenylamine (16 mmoles) and 4.28 g of lithium iodide (32 mmoles); the reaction was carried out at 200° C. for 0.42 hour. Run C, which is a control run for comparison purposes, contained 3.56 g of iodine (14 mmoles) and 8.07 g of triphenylphosphine (30.8 mmoles); the reaction was carried out at 180° C. for about 4 hours. Run C showed acetaldehyde formation upon analysis of the reaction products produced at a considerably slower rate; the amount produced after 4 hours was appreciably less than was produced in Runs A and B at much shorter reaction times. The results are summarized below:

| RUN | A | B | C |
|---|---|---|---|
| Acetaldehyde, mole | 0.36 | 0.24 | 0.1 |
| Paraldehyde, mole | 0.01 | 0.06 | 0 |
| Acetic acid, mole | 0.41 | (b) | (b) |
| Methane, mole | 0.02 | 0.04 | 0.03 |
| Ethyl acetate, mole | 0.04 | 0.02 | 0.02 |
| Rate (a) | 2.72 | 6.9 | 0.2 |

(a) gmoles/L/hr to acetaldehyde, includes acetaldehyde equivalents in paraldehyde
(b) not analyzed The results show the importance of the use of lithium iodide as the iodine source in the reaction. In its absence and the use of elemental iodine as the iodine source, acetaldehyde was produced at much slower rates. This clearly establishes the criticality of lithium iodide for the selective production of acetaldehyde and the fact that one cannot successfully employ any iodine source.

EXAMPLE 7

The autoclave was charged with 1.02 g of [RuCl$_2$(CO)$_3$]$_2$ (2.0 m moles) 4.28 g LiI (32.0 mmoles) and 150 ml of methyl acetate were reacted at 180° C. and 5000 psi (H$_2$:CO=0.67) in a manner as described in Example 1. The consumption of 3000 psi required 39 minutes. Analysis indicated the following products were produced:

| | moler |
|---|---|
| Acetaldehyde | 0.14 |
| Paraldehyde | 0.02 |
| Acetic acid | 0.16 |
| Methane | 0.03 |
| Water | 0.06 |
| Ethanol | 0.06 |
| Ethyl acetate | 0.03 |

The rate to acetaldehyde was 2.13 g moles/L/hr (includes acetaldehyde equivalent in paraldehyde) and the selectivity was 63%. The example demonstrates that Group VIII metals other than cobalt will catalyze the reaction.

EXAMPLE 8

A series of experiments was carried out under conditions similar to Example 1 but with the exception that different ester feedstocks were utilized. Catalyst A consists of 2.5 g cobalt iodide (8.0 mmoles), 4.28 g of lithium iodide (32.0 mmoles) and 2.95 g of tributylamine (16.0 mmoles). Catalyst B consists of 2.5 g cobalt iodide (8.0 mmoles), 4.28 gm LiI (32.0 mmoles) and 3.95 g of triphenylamine. All runs were carried out at 5000 psi ($H_2$:CO=1:1). The results are summarized below:

| Ester Feedstock | Moles charged | Catalyst | Temp. °C. | Products[a], Moles | | | | Acetaldehyde Rate gmole/L/hr. |
| | | | | $CH_3CHO$ | $CH_4$ | $H_2O$ | $C_6H_{12}O_3$[b] | |
| --- | --- | --- | --- | --- | --- | --- | --- | --- |
| Methyl Isobutyrate | 0.87 | A | 180 | 0.12 | 0.03 | 0.2 | ND | 0.5 |
| Dimethyl Succinate | 0.64 | B | 180 | 0.15 | 0.02 | 0.02 | ND | 1.02 |
| Dimethyl Malonate | 1.31 | B | 180 | 0.03 | 0.02 | 0.06 | ND | 0.3 |
| Dimethyl Phthalate | 1.3 | A | 180 | 0.19 | 0.02 | 0.07 | ND | 0.4 |
| Methyl Propionate | 1.56 | A | 180 | 0.1 | 0.01 | 0.05 | 0.08 | 4.01 |
| Methyl Propionate | 1.56 | B | 200 | 0.16 | 0.04 | 0.05 | 0.07 | 5.1 |
| Methyl Salicylate | 1.15 | B | 180 | 0.23 | 0.01 | 0.08 | ND | 5.36 |
| Methyl Formate | 2.4 | B | 180 | 0.12 | 0.02 | 0.05 | ND | 0.3 |

[a]The expected carboxylic acid was detected; however, the exact amount was not determined.
[b]$C_6H_{12}O_3$ = paraldehyde
ND - Not determined.

EXAMPLE 9

The autoclave was charged with 2.5 g of cobaltous iodide (8 mmoles), 3.92 g of triphenylamine (16 mmoles), 4.28 g of lithium iodide (32 mmoles), 50 ml of diphenyl ether as a solvent and 100 ml of trimethyl borate (0.89 mole). The reactor contents were heated to 200° C. and the pressure adjusted to 5000 psig. Consumption of 3000 psi required 1.75 hours. Acetaldehyde was the principal product with lesser amounts of dimethylacetal, methyl acetate and ethanol formed.

EXAMPLE 10

The autoclave was charged with 2.06 g of rhodium dicarbonylacetyl-acetonate (8 mmoles), 4.28 g of lithium iodide (32 mmoles), 1.5 ml of methyl iodide (24 mmoles) and 150 ml of trimethyl borate (1.33 moles). The reactor contents were heated to 180° C. and the pressure adjusted to 1500 spig. Consumption of 2500 psi required one hour. Acetaldehyde was the principal product.

We claim:

1. A process for the reaction of an inorganic or organic ester with carbon monoxide or synthesis gas at a temperature of from 100° C. to 300° C., a pressure of from 500 psig to 10,000 psig, a $H_2$:CO mole ratio in the synthesis gas of from 1:10 to 10:1, in contact with an Me homogenous catalyst system containing lithium iodide as the promoter, wherein the mole ratio of LiI:Me is from 50:1 to 1:50 to selectively produce an aldehyde, wherein Me is cobalt, rhodium or ruthenium.

2. A process as claimed in claim 1 wherein Me is cobalt.

3. A process as claimed in claim 1 wherein Me is rhodium.

4. A process as claimed in claim 1 wherein Me is ruthenium.

5. A process as claimed in claim 1 wherein the temperature is from 150° C. to 225° C., the pressure is from 1,000 psig to 6,000 psig and the $H_2$:CO mole ratio is from 2:1 to 1:2.

6. A process as claimed in claim 1 wherein the mole ratio of LiI:Me is from 10:1 to 1:10.

7. A process as claimed in claim 1 wherein the mole ratio of LiI:Me is from 3:1 to 5:1.

8. A process as claimed in claim 1 wherein said organic ester has the structural formula RCOOR' or R'OOCR"COOR' in which R and R' are monovalent hydrocarbyl (i) alkyl groups having from 1 to 30 carbon atoms, (ii) alkenyl groups having from 2 to 30 carbon atoms, or (iii) aryl, aralkyl or alkaryl groups having from 6 to 10 ring carbon atoms and from 1 to 10 carbon atoms in the alk-moiety thereof, and R" is a divalent hydrocarbyl group as defined for R and R' having from 2 to 10 carbon atoms; R can also be hydrogen.

9. A process as claimed in claim 1 wherein said organic ester is methyl acetate.

10. A process as claimed in claim 7 wherein said organic ester is methyl acetate.

11. A process as claimed in claim 1 wherein said inorganic ester has the formula B(OR"")$_3$ in which B is boron and R"" is an alkyl group having from 1 to 15 carbon atoms.

12. A process as claimed in claim 1 wherein said inorganic ester is trimethyl borate.

13. A process as claimed in claim 1 wherein an organic ligand of the formula ER$_3$''' is present, wherein E is nitrogen, phosphorus, arsenic, antimony and bismuth and R''' is an organic moiety.

14. A process as claimed in claim 8 wherein an organic ligand of the formula ER$_3$''' is present, wherein E is nitrogen, phosphorus, arsenic, antimony and bismuth and R''' is an organic moiety.

15. A process as claimed in claim 9 wherein an organic ligand of the formula ER$_3$''' is present, wherein E is nitrogen, phosphorus, arsenic, antimony and bismuth and R''' is an organic moiety.

16. A process as claimed in claim 11 wherein an organic ligand of the formula ER$_3$''' is present, wherein E is nitrogen, phosphorus, arsenic, antimony and bismuth and R''' is an organic moiety.

17. A process as claimed in claim 13 wherein said ligand is a tertiary amine.

18. A process as claimed in claim 14 wherein said ligand is a tertiary amine.

19. A process as claimed in claim 15 wherein said ligand is a tertiary amine.

20. A process as claimed in claim 16 wherein said ligand is a tertiary amine.

21. A process as claimed in claim 13 wherein said ligand is a phosphine.

22. A process as claimed in claim 14 wherein said ligand is a phosphine.

23. A process as claimed in claim 15 wherein said ligand is a phosphine.

24. A process as claimed in claim 16 wherein said ligand is a phosphine.

* * * * *